(12) United States Patent
Huang et al.

(10) Patent No.: US 11,464,450 B2
(45) Date of Patent: Oct. 11, 2022

(54) FIXED-SENSOR FINGER ACTION DETECTING GLOVE

(71) Applicant: REHABOTICS MEDICAL TECHNOLOGY CORP., Jhubei (TW)

(72) Inventors: Jian-Jia Huang, Jhubei (TW); Shu-Wei Pu, Jhubei (TW); Tsung-Fu Liu, Jhubei (TW); Pin-Tseng Liu, Jhubei (TW); Li-Wei Cheng, Jhubei (TW)

(73) Assignee: REHABOTICS MEDICAL TECHNOLOGY CORP., Jhubei (TW)

( * ) Notice: Subject to any disclaimer, the term of this patent is extended or adjusted under 35 U.S.C. 154(b) by 957 days.

(21) Appl. No.: 16/235,714

(22) Filed: Dec. 28, 2018

(65) Prior Publication Data

US 2019/0209086 A1 Jul. 11, 2019

(30) Foreign Application Priority Data

Jan. 5, 2018 (TW) .................................. 107100530

(51) Int. Cl.
*A61B 5/00* (2006.01)
*G06F 3/00* (2006.01)
(Continued)

(52) U.S. Cl.
CPC .......... *A61B 5/6806* (2013.01); *A61B 5/1126* (2013.01); *A61B 5/6826* (2013.01); *A61F 5/013* (2013.01); *A61F 5/0118* (2013.01); *A61H 1/0288* (2013.01); *A61H 3/00* (2013.01); *A63B 23/16* (2013.01); *B25J 9/0006* (2013.01);
(Continued)

(58) Field of Classification Search
CPC . A61B 5/6806; A61B 5/6826; A61B 2505/09; A61F 5/0118; A61F 5/013; A61H 1/0288; A61H 3/00; A61H 2201/1635; A61H 2201/165; A61H 2201/5058; A61H 2205/067; A61H 2205/065; A63B 23/16; B25J 9/0006; G06F 3/014
See application file for complete search history.

(56) References Cited

U.S. PATENT DOCUMENTS 5,442,729 A * 8/1995 Kramer ................... G06F 3/014
600/595
6,325,768 B1 * 12/2001 Williams ............. A61B 5/4528
600/595

(Continued)

*Primary Examiner* — Samchuan C Yao
*Assistant Examiner* — Tyler A Raubenstraw
(74) *Attorney, Agent, or Firm* — Rabin & Berdo, P.C.

(57) ABSTRACT

A fixed-sensor finger action detecting glove has a glove body, five covering sheets, five fixing bases, five sensors, and five fixing assemblies. A side of the glove body forms a hand back section and five finger back sections. The covering sheet is mounted on the finger back section and forms a passage. The fixing base is made from a flexible material, is mounted through the passage, and has two limiting walls. The sensor is located in the passage between the two limiting walls, preventing the sensor from deviating. The fixing assembly is mounted between an end of the sensor and an end of the finger back section, detachably connects the sensor and the finger back section, and prevents the sensor from moving back and forth. Thus, the fixed-sensor finger action detecting glove is capable of detecting actions of the fingers precisely.

16 Claims, 6 Drawing Sheets

(51) Int. Cl.
*A63B 23/16* (2006.01)
*G06F 3/01* (2006.01)
*A61F 5/01* (2006.01)
*A61B 5/11* (2006.01)
*B25J 9/00* (2006.01)
*A61H 3/00* (2006.01)
*A61H 1/02* (2006.01)

(52) U.S. Cl.
CPC ......... *G06F 3/014* (2013.01); *A61B 2505/09* (2013.01); *A61H 2201/165* (2013.01); *A61H 2201/1635* (2013.01); *A61H 2201/5058* (2013.01); *A61H 2205/067* (2013.01)

(56) References Cited

U.S. PATENT DOCUMENTS

| | | | | |
|---|---|---|---|---|
| 6,701,296 | B1* | 3/2004 | Kramer | G06F 1/163 |
| | | | | 370/545 |
| 9,387,112 | B2* | 7/2016 | Bryant | A61F 5/013 |
| 9,918,504 | B1* | 3/2018 | Johnson | A41D 19/0017 |
| 9,993,891 | B2* | 6/2018 | Wiryadinata | B23K 9/0956 |
| 2010/0234182 | A1* | 9/2010 | Hoffman | A61F 5/013 |
| | | | | 482/8 |
| 2012/0029399 | A1* | 2/2012 | Sankai | A61H 1/0288 |
| | | | | 601/40 |
| 2012/0144554 | A1* | 6/2012 | Thellmann | A63B 71/0622 |
| | | | | 2/161.1 |
| 2012/0157263 | A1* | 6/2012 | Sivak | G16H 40/63 |
| | | | | 482/4 |
| 2014/0257159 | A1* | 9/2014 | Kelly | A61F 5/0118 |
| | | | | 602/21 |
| 2015/0141206 | A1* | 5/2015 | James, Jr. | A63B 21/4019 |
| | | | | 482/47 |
| 2015/0374575 | A1* | 12/2015 | Kamper | A61F 5/013 |
| | | | | 601/40 |
| 2016/0089571 | A1* | 3/2016 | Wesley | A61B 5/1071 |
| | | | | 482/8 |
| 2016/0161301 | A1* | 6/2016 | Guenther | A61B 5/6825 |
| | | | | 702/150 |
| 2016/0162022 | A1* | 6/2016 | Seth | G06F 3/014 |
| | | | | 345/156 |
| 2016/0193101 | A1* | 7/2016 | Pu | A61F 2/70 |
| | | | | 623/24 |
| 2017/0215495 | A1* | 8/2017 | Okumiya | A41D 19/0013 |
| 2017/0266075 | A1* | 9/2017 | Becchi | A63B 23/16 |
| 2017/0319430 | A1* | 11/2017 | Shadduck | G05G 9/04 |
| 2018/0193699 | A1* | 7/2018 | DeBates | A61B 5/224 |
| 2018/0263563 | A1* | 9/2018 | McMillen | G06F 3/014 |
| 2018/0303698 | A1* | 10/2018 | Wijesundara | F15B 15/10 |
| 2018/0340847 | A1* | 11/2018 | Pan | B32B 27/12 |
| 2018/0364804 | A1* | 12/2018 | Hoen | G06F 3/014 |
| 2019/0038222 | A1* | 2/2019 | Krimon | A61B 5/1107 |
| 2019/0099123 | A1* | 4/2019 | Zambriski | A61B 5/7445 |
| 2019/0133463 | A1* | 5/2019 | Kobayashi | B06B 1/06 |

* cited by examiner

FIXED-SENSOR FINGER ACTION DETECTING GLOVE

BACKGROUND OF THE INVENTION

1. Field of the Invention

The present invention relates to a finger action sensing glove, especially to a finger action sensing glove that is used with rehabilitation apparatuses.

2. Description of the Prior Arts

Among the rehabilitation apparatuses, a hand exoskeleton is designed for finger rehabilitation. The hand exoskeleton is mounted on the back of the patient's hand by a mechanical structure and sleeved on the patient's fingers. By this, the hand exoskeleton facilitates the patient's fingers to do necessary exercises for rehabilitation.

Figure 6:
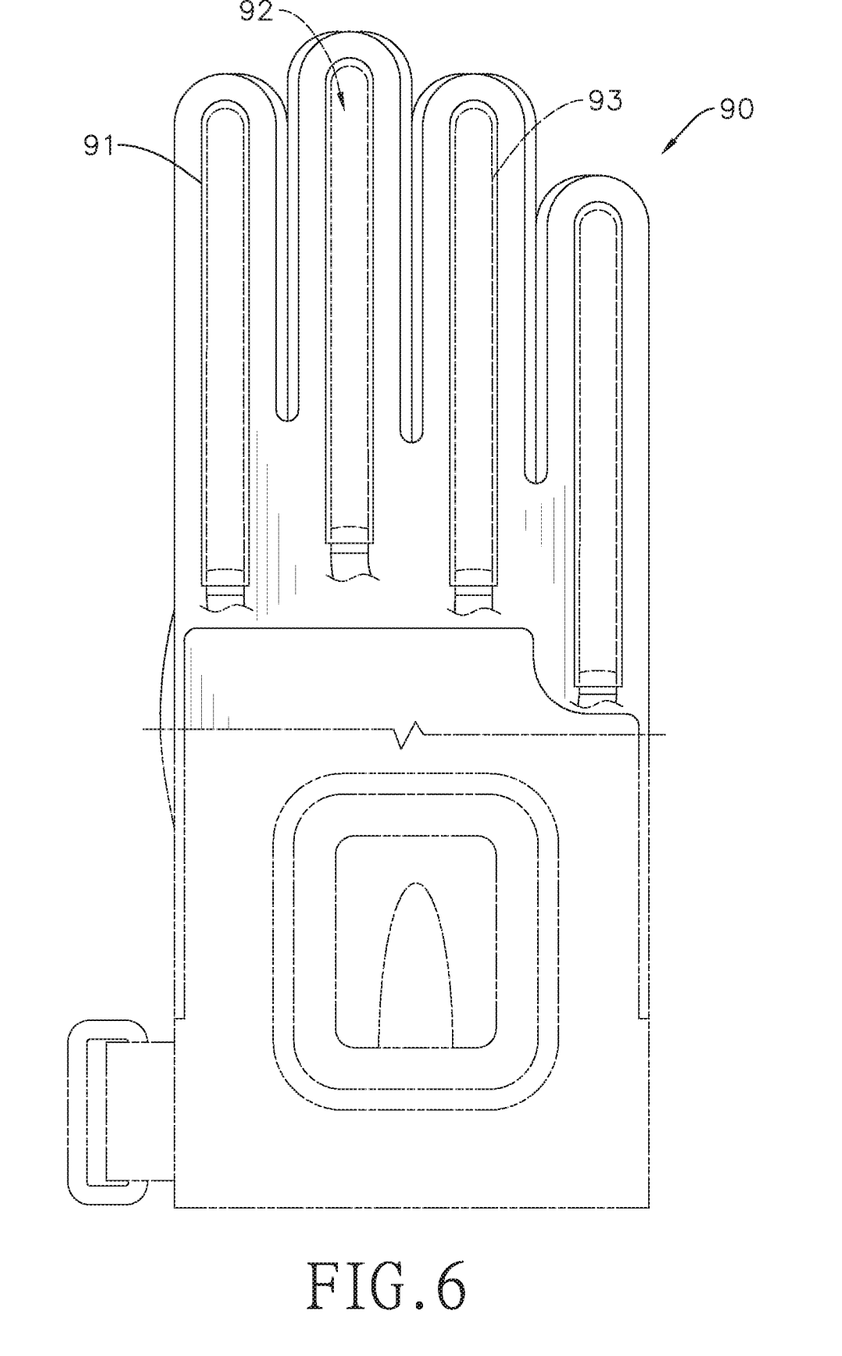
FIG. 6 is a top view of the sensing glove in accordance with the prior art.

The abovementioned hand exoskeleton can be used further with a finger action sensing glove. With reference to FIG. 6, five elongated clothes 91 are sewed on a back of finger sections of the finger action sensing glove 90. The clothes 91 extend to ends of the finger sections respectively. Each of the clothes 91 covers and forms a passage 92 with the back of the finger sections of the finger action sensing glove 90. A sensor 93 in a strip shape is mounted in the passage 92. By this, when the user moves the fingers, the sensor 93 detects the actions of the fingers and simultaneously sends a signal to the abovementioned hand exoskeleton. Then, the hand exoskeleton facilitates the patient's fingers to do the same actions as the finger action sensing glove 90. With the finger action sensing glove 90 and the hand exoskeleton, the therapists are able to assist the patients in rehabilitation, or the patients are able to do mirror therapy by their own hands.

However, the disadvantage of the conventional finger action sensing glove 90 is that the sensor 93 is only placed in the passage 92 but not fixed to the clothes 91 or the finger action sensing glove 90. Thus, when the finger is bending, the end of the sensor 93 may move back toward the wrist relative to the passage 92, or the whole sensor 93 may deviate left and right relative to the passage 92. The abovementioned situations both make the finger action sensing glove 90 unable to sense the actions of the fingers precisely, so the user will not be able to control the hand exoskeleton by the finger action sensing glove 90 precisely. Therefore, the conventional finger action sensing glove 90 still needs improvement.

To overcome the shortcomings, the present invention provides a fixed-sensor finger action detecting glove to mitigate or obviate the aforementioned problems.

SUMMARY OF THE INVENTION

The main objective of the present invention is to provide a fixed-sensor finger action detecting glove that fixes the sensor's end in order to prevent the sensor form moving back and forth, and also restrict the sensor from deviating left and right.

The fixed-sensor finger action detecting glove has a glove body. The glove body has a side surface, a hand back section, and five finger back sections. The hand back section is formed on the side surface of the glove body. The five finger back sections are formed on the side surface of the glove body and connect to the hand back section. A sensing assembly is mounted on the hand back section of the glove body. Multiple covering sheets are mounted on the finger back sections respectively. Each one of the covering sheets and the corresponding finger back section form a passage surrounded by the covering sheet and the finger back section, and the passage having two openings on two ends thereof, respectively. Multiple fixing bases are mounted in the passages respectively and are made of a flexible material. Each one of the fixing bases is in a strip shape and has two limiting walls. The two limiting walls are spaced apart and extend along the corresponding passage. Multiple sensors are mounted through the passages respectively. Each one of the sensors is in a strip shape and is located between the two limiting walls of the fixing base in the corresponding passage. The two ends of each one of the sensors are an inner end and an outer end, respectively. The inner end connects to the sensing assembly. Multiple fixing assemblies correspond in position to the sensors respectively. Each one of the fixing assemblies has a first fixing unit and a second fixing unit. The first fixing unit is mounted on the outer end of the corresponding sensor. The second fixing unit is mounted on an end of the finger back section corresponding to said sensor. The first fixing unit and the second fixing unit are detachably combined with each other.

Each sensor is mounted through the respective passage formed by the covering sheet and extends to the end of the finger. The first fixing unit and the second fixing unit, which are combined with each other detachably, are mounted between the outer end of the sensor and an end of the finger back section of the glove body. Therefore, the present invention is capable of fixing the outer end of the sensor securely to prevent the sensor from moving back and forth. In addition, by mounting a fixing base in the passage and mounting the sensor between the two limiting walls of the fixing base, the present invention prevents the sensor from deviating left and right. Thus, the present invention fixes the sensor in the front-back direction as well as the left-right direction so that the present invention is able to sense the actions of the fingers precisely.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
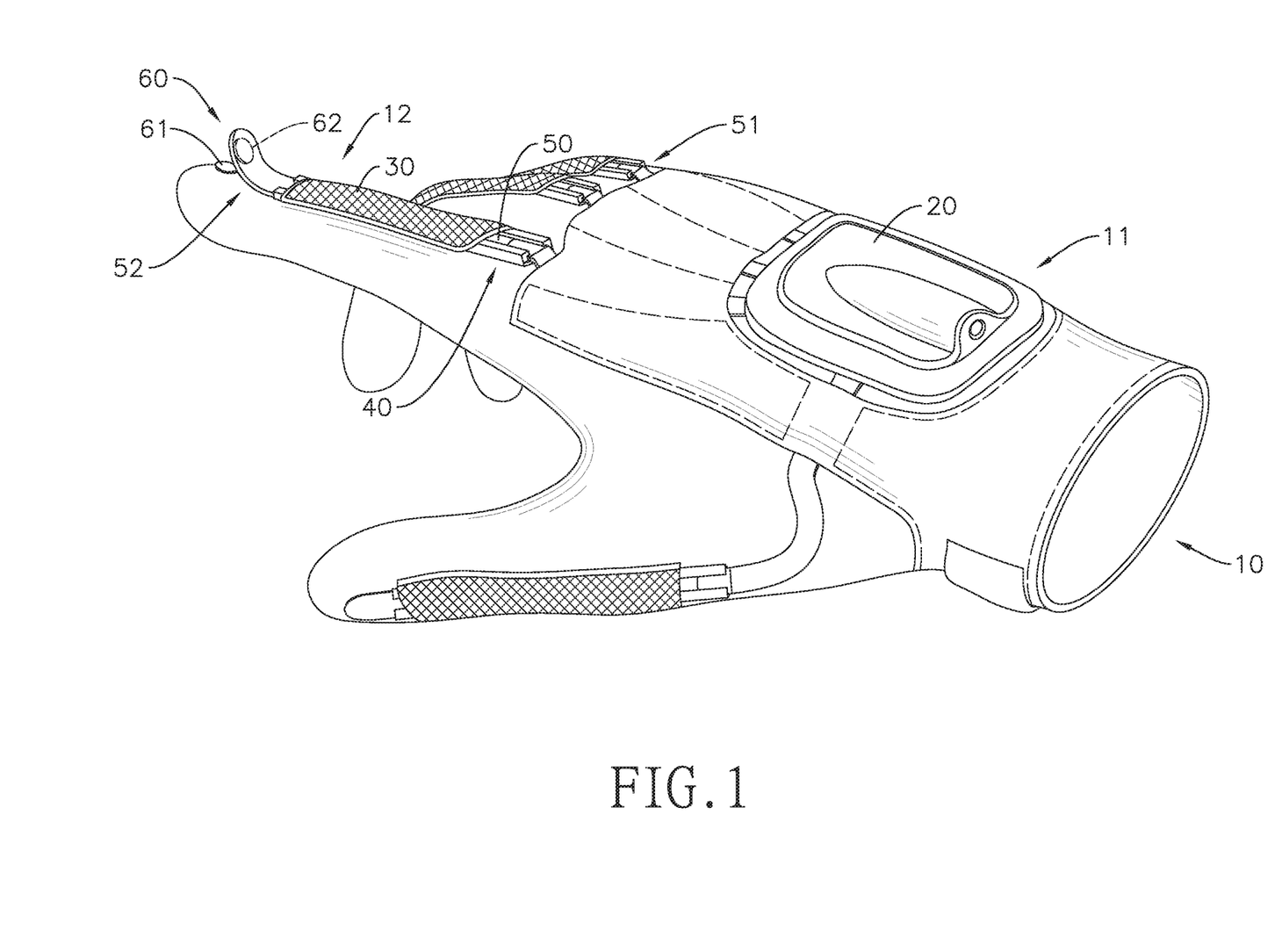
FIG. 1 is a perspective view of a fixed-sensor finger action detecting glove in accordance with the present invention.
Figure 2:
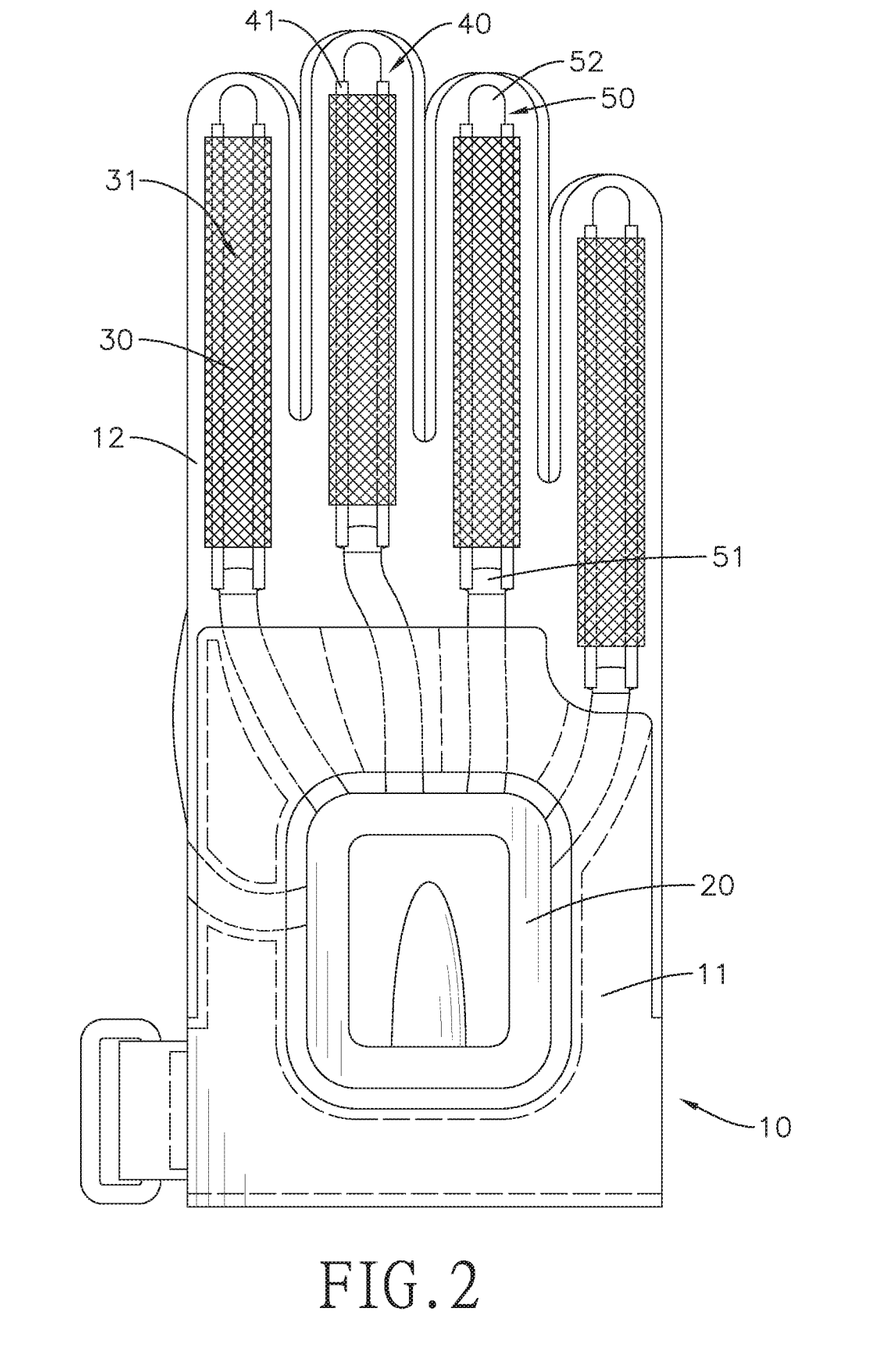
FIG. 2 is a schematic back view of the fixed-sensor finger action detecting glove in FIG. 1, showing the hand back section.

With reference to FIGS. 1 and 2, a fixed-sensor finger action detecting glove in accordance with the present invention comprises a glove body 10, a sensing assembly 20, multiple covering sheets 30, multiple fixing bases 40, multiple sensors 50, and multiple fixing assemblies 60.

In a preferred embodiment, there are five said covering sheets 30, five said fixing bases 40, five said sensors 50, and five said fixing assemblies 60, but the numbers of these elements are not limited to the abovementioned. The number of the covering sheets 30 can also be more than that of the fixing bases 40. That is, the manufacturer can reserve multiple covering sheets 30 and let the user decide which covering sheet 30 should have a fixing base 40 mounted therein. Furthermore, the number of the fixing bases 40 can also be more than that of the sensors 50. Likewise, the manufacturer can reserve multiple fixing bases 40 and let the user decide which fixing base 40 should have a sensor 50 mounted therein. The number of the sensors 50 can be less than five. The number of the sensors 50 mainly depends on how many fingers need controlling.

Figure 3:
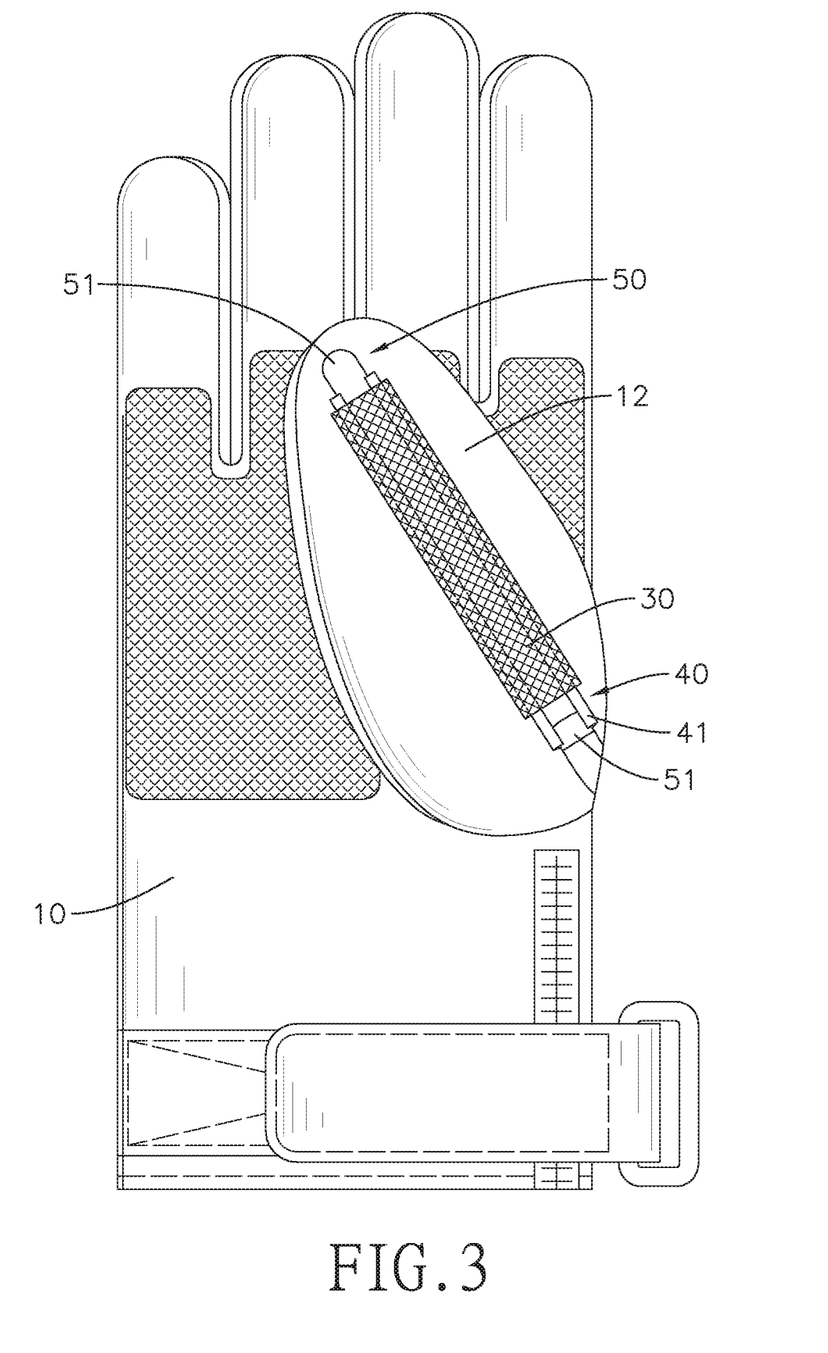
FIG. 3 is a schematic front view of the fixed-sensor finger action detecting glove in FIG. 1, showing the palm.

With reference to FIGS. 1 to 3, a side of the glove body 10 forms a hand back section 11 and five finger back sections 12. The five finger back sections 12 are connected to the hand back section 11. Specifically, the glove body 10 forms two side surfaces when the glove body 10 is worn by a user. One of the side surfaces corresponds to the palm of the user, and the other side surface corresponds to the back of the hand of the user. The abovementioned hand back section 11 and the abovementioned finger back section 12 are both formed on the side surface that corresponds to the back of hand of the user who wears the glove body 10.

The sensing assembly 20 is mounted on the hand back section 11 of the glove body 10. In a preferred embodiment, the sensing assembly 20 includes a circuit board and a chip. The sensing assembly 20 can be a processing unit which processes information, or the sensing assembly 20 can also be a device which only transmits and receives information. Alternatively, the sensing assembly 20 can also be a device that contains both of the features, but the sensing assembly 20 is not limited to a circuit board or a chip.

Figure 4:
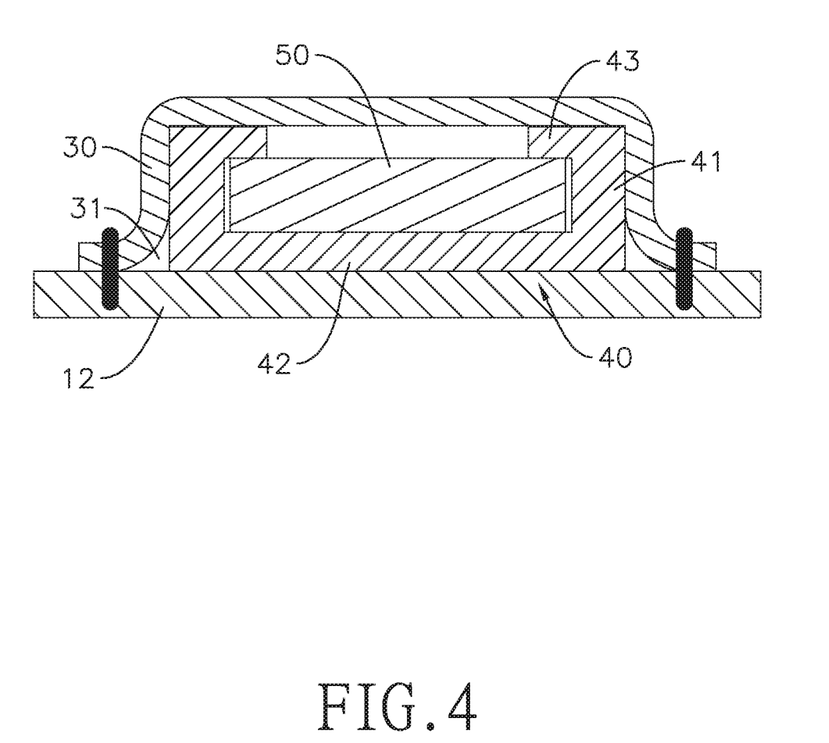
FIG. 4 is a side view in cross section of the fixed-sensor finger action detecting glove in FIG. 1, showing the connection between the covering sheet, the fixing base, the finger back section, and the sensor.

With reference to FIGS. 2 and 4, the abovementioned five covering sheets 30 are mounted on the five finger back sections 12 respectively. Each one of the covering sheets 30 and the corresponding finger back section 12 together form a passage 31 surrounded by the covering sheet 30 and the finger back section 12, and the passage 31 has two openings on two ends respectively. One of the openings faces the sensing assembly 20, and the other opening faces an end of the finger back sections 12. Specifically, in a preferred embodiment, the covering sheets 30 are in a strip shape, and two sides of each one of the covering sheets 30 are sewed on the corresponding finger back section 12. The way of fixing the covering sheets 30 is not limited to sewing, but also can be riveting or hot pressing, as long as the two elongated sides of the covering sheets 30 are fixed and the covering sheets 30 and the finger back sections 12 cover and form the elongated passage 31. In addition, in a preferred embodiment, the covering sheets 30 are made from, but not limited to, cloth. The covering sheets 30 can also be made from flexible plastic, as long as the material of the covering sheets 30 facilitates the covering sheets 30 to cover and form the passage 31 in a long strip shape.

With reference to FIGS. 2 and 4, the abovementioned five fixing bases 40 are mounted in the five passages 31 formed by the covering sheets 30, respectively. Each one of the fixing bases 40 is in a strip shape, and each one of the fixing bases 40 has two limiting walls 41, a baseboard 42, and two stopping sheets 43. The two limiting walls 41 are spaced apart. The two limiting walls 41 protrude from two sides of the baseboard 42 respectively. In other words, the two opposite sides of the baseboard 42 are connected to the two bottom sides of the two limiting walls 41 respectively. The two stopping sheets 43 are formed on the tops of the two limiting walls 41 respectively and bend toward each other. The limiting walls 41, the baseboard 42, and the stopping sheets 43 all extend along the corresponding passage 31. Besides, in a preferred embodiment, the lengths of the limiting walls 41, the baseboard 42, and the stopping sheets 43 are all the same, and the limiting walls 41, the baseboard 42, and the stopping sheets 43 all protrude out of the two openings of the passage 31. However, the lengths of the three components and the relationship between the three components and the passage 31 are not limited to the abovementioned. In addition, the baseboard 42 can also be connected between two top sides of the two limiting walls 41 to be a top board. The two stopping sheets 43 can also be formed and bending on two bottom sides of the two limiting walls 41, respectively. Furthermore, the fixing bases 40 can also be implemented without the two stopping sheets 43. In this case, the fixing bases 40 can still prevent the sensors 50 from deviating left and right by the two limiting walls 41. In addition, in a preferred embodiment, two sides of each one of the fixing bases 40 are attached to the covering sheet 30 so that each one of the fixing bases 40 is fixed securely on the left-right side in the passage 31 of the covering sheet 30. The relationship between the fixing bases 40 and the covering sheet 30 is not limited to the abovementioned. Alternatively, there can also be a gap between the two sides of each one of the fixing bases 40 and the covering sheet 30.

Besides, the fixing bases 40 are made from a flexible material with flexibility and extensibility that can sustain bending without permanent deformation. Also, the material has a certain level of supporting strength so that it has a better limiting effect than cloth. More specifically, the fixing bases 40 are made from, but not limited to, flexible plastic.

With reference to FIGS. 1, 2 and 4, the five sensors 50 are mounted through the five passages 31 formed by the five covering sheets 30, respectively. Each one of the sensors 50 is in a strip shape and is located between the two limiting walls 41 of the corresponding fixing base 40 in the corresponding passage 31. Specifically, in a preferred embodiment, each one of the sensors 50 is mounted on the corresponding baseboard 42, and the two stopping sheets 43 abut the top surface of the corresponding sensor 50. That is, the baseboard 42 and the two stopping sheets 43 clamp the sensor 50. However, the relationship between the sensor 50, the baseboard 42 and the two stopping sheets 43 is not limited to the abovementioned. In another embodiment which is implemented without the two stopping sheets 43, the sensor 50 is mounted on the baseboard 42, and the top surface of the sensor 50 selectively abuts the covering sheet 30. In still another preferred embodiment wherein the baseboard 42 is replaced with a top board, the sensor 50 is clamped between the top board and the finger back section 12.

In addition, the two ends of each one of the sensors 50 are an inner end 51 and an outer end 52, respectively. The inner end 51 is connected to the sensing assembly 20. The outer end 52 passes through the passage 31 and is located on the end of the finger back section 12. The sensor 50 is capable of detecting the change of curvature during bending and simultaneously sends information to the sensing assembly 20. Then, the sensing assembly 20 will process or transmit the information to sense the actions of the fingers.

With reference to FIG. 1, the fixing assemblies 60 correspond in position to the sensors 50 respectively. Each one of the fixing assemblies 60 has a first fixing unit 61 and a second fixing unit 62. The first fixing unit 61 is mounted on the outer end 52 of the corresponding sensor 50. The second fixing unit 62 is mounted on an end of the finger back section 12 corresponding to said sensor 50. The first fixing unit 61 and the second fixing unit 62 are combined with each other detachably. Specifically, in a preferred embodiment, each one of the fixing assemblies 60 is a snap button. More specifically, the first fixing unit 61 is a stud and the second fixing unit 62 is a socket. The structure of the fixing assembly 60 is not limited to the abovementioned, as the first fixing unit 61 can be a socket and the second fixing unit 62 can be a stud. Besides, the fixing assembly 60 is not limited to a snap button. For example, the fixing assembly 60 can also be an adhesive strap (hook-and-loop fastener). Thus, the end of the finger back section 12 is part of the adhesive strap. That is, the end of the finger back section 12 is the second fixing unit 62. By this, the first fixing unit 61 and the second fixing unit 62 are capable of achieving the same effect of combining with each other detachably. Furthermore, the first fixing unit 61 can also be a hole formed on the outer end 52 of the sensor 50, and then the second fixing unit 62 will be a hook hooking the first fixing unit 61. By this, the first fixing unit 61 and the second fixing unit 62 are capable of achieving the same effect of combining with each other detachably.

Figure 5:
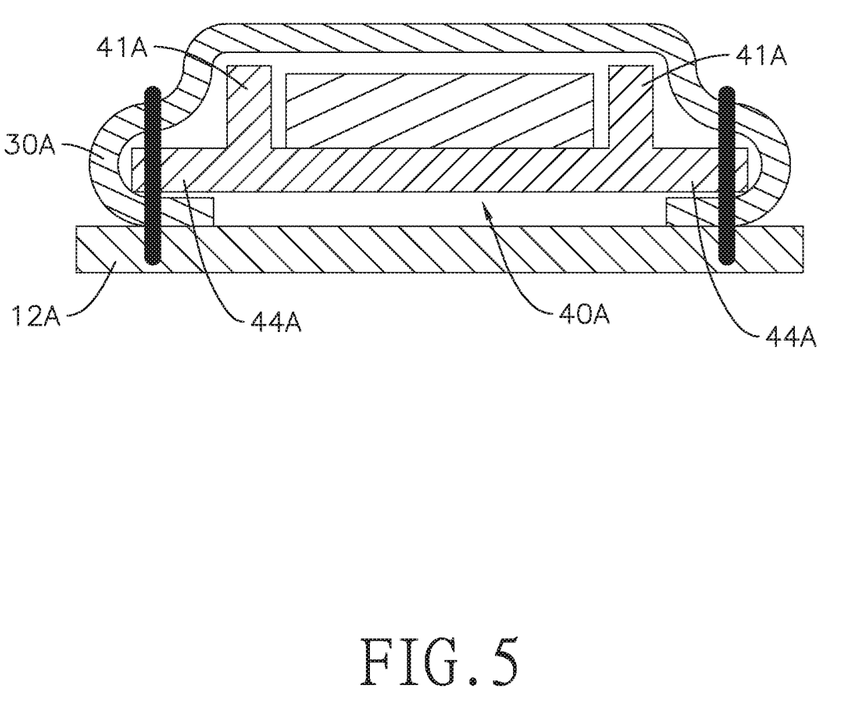
FIG. 5 is a side view in cross section in the second embodiment of the fixed-sensor finger action detecting glove in FIG. 1.

With reference to FIG. 5, the second embodiment of the present invention is substantially same as the first embodiment. The differences between the first embodiment and the second embodiment are as follows.

Each of the fixing bases 40 further comprises two combination sections 44A. The two combination sections 44A protrude from two outer sides of the two limiting walls 41 respectively. Two sides of the corresponding covering sheet 30 are combined with the two combination sections 44A respectively. In other words, in the second embodiment, the fixing base 40A is mounted securely on the finger back section 12A by the combination section 44A, and the two combination sections 44A are combined with the corresponding finger back section 12 together with the covering sheet 30. Specifically, the covering sheets 30A are sewed on the corresponding finger back section 12A with the two corresponding combination sections 44A. However, the combination method of the covering sheet 30A, the combination section 44A, and the finger back section 12A is not limited to sewing, and can also be riveting or hot pressing.

More specifically, in the second embodiment, two sides of each one of the covering sheets 30A bend and extend to a bottom surface of the corresponding fixing base 40A, and the two sides of each one of the covering sheets 30A are mounted between the fixing base 40A and the corresponding finger back section 12A. In this way, the covering sheet 30A separates the fixing base 40A and the finger back section 12A. But, the relationship between the covering sheet 30A, the fixing base 40A, and the finger back section 12A is not limited to the abovementioned.

In addition, in the second embodiment, each one of the covering sheets 30A further comprises two top segments. The two sides of each one of the covering sheets 30A are formed on the two top segments respectively. The two top segments are located at tops of the two combination sections 44A respectively as the two sides of each one of the covering sheets 30A are located at a bottom of the two combination sections 44A respectively. Each one of the top segments is sewed together with the corresponding combination section 44A, the corresponding side of the covering sheet 30A, and the finger back section 12A. However, the structure is not limited to the abovementioned, as the combination section 44A, the side of the covering sheet 30A, and the finger back section 12A can also be sewed together without the top segment.

As the finger is moving and bending the sensor 50, the outer end 52 of the sensor 50 is fixed securely on the finger back section 12 by the fixing assembly 60 so that the sensor 50 will not move back and forth even when the finger is bending. In addition, the two limiting walls 41 of the fixing base 40 which are located on the two sides of the sensor 50 are able to restrict the sensor 50 from deviating left and right, respectively. Therefore, the present invention fixes the sensor, preventing deviations in the front-back direction as well as the left-right direction so that the present invention is able to sense the actions of the fingers precisely.

When in use, the present invention cooperates with a hand exoskeleton. The present invention is worn in the same way as a general-purpose glove. The user moves the fingers after putting on the present invention, and then the sensors 50 will be bent with the bending of the fingers. The sensors 50 sense the change of the curvature during bending and send information to the sensing assembly 20 simultaneously. Then, the sensing assembly 20 transmits the information to the hand exoskeleton or control the hand exoskeleton directly after processing the information. By the abovementioned procedure, the present invention can sense the actions of the fingers and then make the hand exoskeleton do the same actions synchronously. However, the present invention is not limited to cooperation with rehabilitation apparatuses, as the present invention can also be used in any situation that needs to sense the actions of the fingers.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A fixed-sensor finger action detecting glove comprising:
   a glove body having
     a side surface;
     a hand back section formed on the side surface of the glove body; and
     five finger back sections formed on the side surface of the glove body and connecting to the hand back section;
   a sensing assembly mounted on the hand back section of the glove body;
   multiple covering sheets mounted on the finger back sections respectively; each one of the covering sheets and the corresponding finger back section forming a passage surrounded by the covering sheet and the finger back section, and the passage having two openings on two ends thereof, respectively;
   multiple fixing bases mounted in the passages respectively and being made of a flexible material; each one of the fixing bases being in a strip shape and having two limiting walls spaced apart and extending along the corresponding passage;
   multiple sensors mounted through the passages respectively; each one of the sensors being in a strip shape and located between the two limiting walls of the fixing base in the corresponding passage; two ends of each one of the sensors being an inner end and an outer end respectively, and the inner end connecting to the sensing assembly; and multiple fixing assemblies corresponding in position to the sensors respectively; each one of the fixing assemblies having
- a first fixing unit mounted on the outer end of the corresponding sensor; and
- a second fixing unit mounted on an end of the finger back section corresponding to said sensor; the first fixing unit and the second fixing unit detachably combined with each other.

2. The fixed-sensor finger action detecting glove as claimed in claim 1, wherein each one of the fixing bases further comprises
a baseboard; the two limiting walls protruding upwards from two sides of the baseboard respectively; the corresponding sensor mounted on the baseboard.

3. The fixed-sensor finger action detecting glove as claimed in claim 2, wherein each one of the fixing bases further comprises
two stopping sheets formed on tops of the two limiting walls respectively, bending to each other, and abutting a top surface of the corresponding sensor.

4. The fixed-sensor finger action detecting glove as claimed in claim 1, wherein each one of the fixing bases further comprises
two combination sections protruding from two outer side surfaces of the two limiting walls respectively, combined with two sides of the corresponding covering sheet respectively, and combined with the corresponding finger back section.

5. The fixed-sensor finger action detecting glove as claimed in claim 3, wherein each one of the fixing bases further comprises
two combination sections protruding from two outer side surfaces of the two limiting walls respectively, combined with two sides of the corresponding covering sheet respectively, and combined with the corresponding finger back section.

6. The fixed-sensor finger action detecting glove as claimed in claim 4, wherein the two sides of each one of the covering sheets are sewed on the corresponding finger back section with the two corresponding combination sections.

7. The fixed-sensor finger action detecting glove as claimed in claim 5, wherein the two sides of each one of the covering sheets are sewed on the corresponding finger back section with the two corresponding combination sections.

8. The fixed-sensor finger action detecting glove as claimed in claim 1, wherein two sides of each one of the covering sheets are sewed on the corresponding finger back section.

9. The fixed-sensor finger action detecting glove as claimed in claim 1, wherein two sides of each one of the covering sheets bend and extend to a bottom surface of the corresponding fixing base, and are mounted between the fixing base and the corresponding finger back section.

10. The fixed-sensor finger action detecting glove as claimed in claim 7, wherein the two sides of each one of the covering sheets bend and extend to a bottom surface of the corresponding fixing base, and are mounted between the fixing base and the corresponding finger back section.

11. The fixed-sensor finger action detecting glove as claimed in claim 1, wherein each one of the fixing bases is made from flexible plastic.

12. The fixed-sensor finger action detecting glove as claimed in claim 10, wherein each one of the fixing bases is made from flexible plastic.

13. The fixed-sensor finger action detecting glove as claimed in claim 1, wherein each one of the fixing assemblies is a snap button.

14. The fixed-sensor finger action detecting glove as claimed in claim 12, wherein each one of the fixing assemblies is a snap button.

15. The fixed-sensor finger action detecting glove as claimed in claim 1, wherein a number of the covering sheets is five; a number of the fixing bases is five; a number of the sensors is five; a number of the fixing assemblies is five.

16. The fixed-sensor finger action detecting glove as claimed in claim 14, wherein a number of the covering sheets is five; a number of the fixing bases is five; a number of the sensors is five; a number of the fixing assemblies is five.

* * * * *